United States Patent [19]

Matsumoto et al.

[11] Patent Number: 4,496,566
[45] Date of Patent: Jan. 29, 1985

[54] NAPHTHYRIDINE DERIVATIVES

[75] Inventors: Jun-ichi Matsumoto, Ikoma; Shinichi Nakamura, Takatsuki, both of Japan

[73] Assignees: Dainippon Pharmaceutical Co., Ltd., Osaka, Japan; Laboratoire Roger Bellon, Neuilly sur Seine, France

[21] Appl. No.: 333,181

[22] Filed: Dec. 21, 1981

[30] Foreign Application Priority Data

Dec. 24, 1980 [JP] Japan ................ 55-184417

[51] Int. Cl.³ ............... A61K 31/495; A61K 31/47; C07D 401/04
[52] U.S. Cl. .................... 514/254; 544/360; 544/362
[58] Field of Search .............. 544/362; 424/250

[56] References Cited

U.S. PATENT DOCUMENTS

| 4,017,622 | 4/1977 | Minami et al. | 544/362 |
| 4,024,255 | 5/1977 | Ellis et al. | 544/362 |
| 4,146,719 | 3/1979 | Irikura et al. | 544/362 |
| 4,292,317 | 9/1981 | Pesson | 544/363 |

FOREIGN PATENT DOCUMENTS

| 0009425 | 4/1980 | European Pat. Off. |
| 55-31042 | 3/1980 | Japan . |
| 55-47658 | 4/1980 | Japan . |
| 2034698 | 6/1980 | United Kingdom | 544/362 |

OTHER PUBLICATIONS

Matsumoto, et al., "Chemical Abstracts", vol. 93, col. 38346a.
"Chemical Abstracts", vol. 93, col. 220772p, 1980.

Primary Examiner—Glennon H. Hollrah
Assistant Examiner—James H. Turnipseed
Attorney, Agent, or Firm—Wenderoth, Lind & Ponack

[57] ABSTRACT

A 1,8-naphthyridine compound of the formula

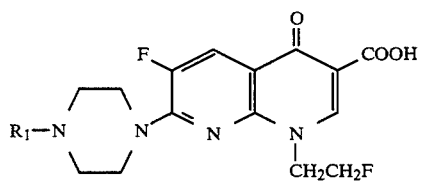

wherein $R_1$ is a lower alkyl group, and the esters and salts thereof.

The 1,8-naphthyridine compound of the formula (I) in which $R_1$ is a methyl group is useful as an antibacterial agent.

3 Claims, No Drawings

NAPHTHYRIDINE DERIVATIVES

This invention relate to novel naphthyridine derivatives having extremely high antibacterial activities, their intermediates, compositions containing these compounds as an active ingredient, and also to their use.

The present invention provides compounds of the following formula

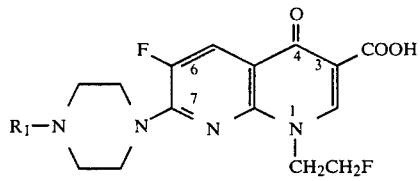
(I)

wherein $R_1$ is a lower alkyl group, the esters and the salts thereof.

In the present specification and appended claims, the term "lower alkyl group" denotes an alkyl group containing 1 to 6 carbon atoms.

The term "esters" of the compounds represented by formula [I] denotes lower alkyl esters such as methyl or ethyl esters; or esters such as pivaloyloxymethyl, ethoxycarbonyloxyethyl, 5-indanyl or phthalidyl esters which can be readily converted to the compounds [I] by chemical hydrolysis or enzymatical hydrolysis in a living body.

The compounds (I) can also exist as a hydrate. Accordingly, the present invention includes the hydrates of the compounds represented by formula [I].

The salts of the compounds [I] denote salts formed between the compounds [I] and acids or bases. The acids may be various inorganic and organic acids, and examples of suitable acids are hydrochloric acid, acetic acid, lactic acid, succinic acid, lactobionic acid, and methanesulfonic acid. The bases may be any inorganic or organic bases capable of forming salts with the carboxyl group of the compounds [I], and examples of suitable bases are metal hydroxides such as sodium or potassium hydroxide, and metal carbonates such as sodium or potassium carbonate.

Among the compounds of the present invention, preferred are those of formula [I] in which $R_1$ is methyl or ethyl. Especially, the compound of formula [I] in which $R_1$ is methyl is most preferred as an antibacterial agent.

It is an object of this invention to provide novel naphthyridine compounds having extremely high antibacterial activities.

Another object of this invention is to provide a composition containing such a novel naphthyridine compound.

These and other objects of this invention become apparent from the following description.

Synthesis and antibacterial activities of various naphthyridine derivatives have previously been reported.

European Patent Application (European Laid-open Patent Application No. 0009425) discloses the following compound which is structurally similar to the compounds of the invention.

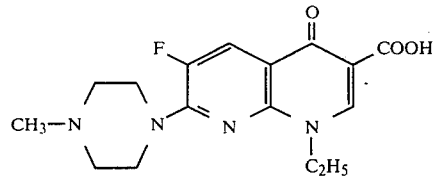

This compound is referred to "compound A" hereinafter.

Japanese Patent Application (Japanese laid-open Patent Application No. 31042/80) discloses the following compound.

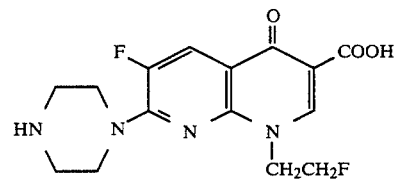

This compound is referred to "compound B" hereinafter.

Now, we have found unexpectedly that a compound which is lower in toxicity than compound A and superior to compound B in in vivo antibacterial activity is obtained by introducing an alkyl group into position 4 of the piperazine ring of the compound B. This discovery has led to the present invention.

The compounds of the present invention can be prepared by reacting a compound of formula [II]

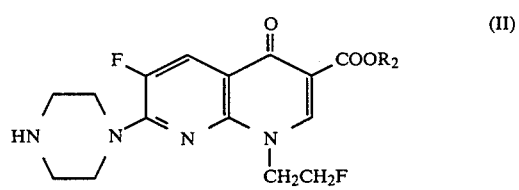
(II)

wherein $R_2$ is a hydrogen atom or a lower alkyl group, with an alkylating agent to introduce the alkyl group into position 4 of the piperazine ring of the compound [II].

Alkylating agents used in this process are selected from lower alkyl halides such as methyl iodide, ethyl iodide, propyl bromide, or butyl bromide; lower alkyl esters of sulfuric acid or sulfonic acid such as dimethyl sulfate, diethyl sulfate or ethyl toluenesulfonate; and lower aliphatic aldehydes such as formaldehyde, acetaldehyde, or isobutyraldehyde, and orthocarboxylic acid trialkyl esters such as ethyl orthoformate in the presence of a reducing reagent. Formic acid is mainly used as the reducing agent. In addition, reducing catalysts such as Raney nickel, palladium, or platinum under hydrogen atomosphere and hydrides such as sodium borohydride or sodium cyanoborohydride may be conveniently employed.

A preferred method of alkylation is the reductive alkylation which involves the reaction of a compound [II] with a lower aliphatic aldehyde in the presence of the reducing reagent mentioned above or the reaction of a compound [II] with a lower aliphatic aldehyde followed by treating the product with the reducing reagent. The former method is especially preferred.

The compounds of this invention can be obtained in good yields by heating a mixture of 1 mole of the compound (II), about 1 mole or a large excess of the aldehyde, and 2 moles or a large excess of formic acid at 80°–120° C. according to the method described above. The compound of this invention in which $R_1$ is methyl is also produced by reacting a compound (II) with a large excess of formaldehyde without an additional reducing reagent.

When the compound is obtained as an ester by the above alkylation process, it can be converted to a compound of formula [I] by hydrolysis in a conventional manner.

On the other hand, if necessary, an ester of the compound [I] may be obtained by esterification of the compound of formula [I] in a conventional manner.

The compounds of the present invention in the form of a salt can be prepared by treating the compound [I] with an acid or a base in a conventional manner.

The starting material [II] in which $R_2$ is hydrogen atom used in this reaction is known and prepared in accordance with a method described in Reference Example given hereinafter.

The starting material [II] in which $R_2$ is a lower alkyl group can be prepared by treating the starting material [II] in which $R_2$ is hydrogen atom with a halogenating agent such as thionylchloride to give a corresponding acid halide followed by treating with a lower alkanol.

The compounds of the present invention prepared by the above mentioned processes can be isolated and purified by usual methods. The compounds may be obtained in the form of a salt, free carboxylic acid or free amine, depending on the conditions of isolation and/or purification. These may be converted to each other to provide the compounds of the present invention in the desired form.

The novel compounds of the invention, as will be shown in Experimental A, B and C given hereinbelow, have excellent antibacterial activities and low toxicity.

Accordingly, the compounds of the invention, especially compound [I] and a non-toxic salt thereof can be used as drugs for the treatment or prevention of bacterial infections of warm-blooded animals including man. Of course, esters of the compound [I] are valuable not only as intermediates for synthesis of the compound [I] but also as antibacterial agents if this ester can be easily transferred to the compound [I] in a living body.

Doses of the compounds of this invention may vary with the age, body weight and conditions of the subjects, the administration route, the number of administrations or the like, but is in the range of 0.3 to 80 mg per kilogram of body weight per day, preferably 1.3 to 50 mg per killogram of body weight per day, for administration to man. The dose may be divided and administered in two to several times per day. The administration route may be oral or parenteral, preferably oral or topical.

The compounds of the present invention can be administered as it is, but usually in the form of a pharmaceutical preparation with pharmaceutical acceptable carries or adjuvants. Specific examples are tablets, capsules, granules, fine granules, powders, syrups, etc. These pharmaceutical preparations are prepared in a customary manner. The adjuvants and carriers are those which are usually used in the field of pharmaceutical preparation and do not react with the compounds of the present invention, such as starch, mannitol, crystalline cellulose, sodium carboxymethylcellulose, or the like.

They may further contain other therapeutically valuable substances according to the purpose of medication.

The pharmaceutical preparation of this invention, for examples tablets and capsules, may contain about 10 to about 700 mg, generally 50 to 500 mg of the compound of this invention, per tablet or capsule. These amounts are not critical, and may be varied according to whether the required amount of the compound of this invention is administered in a single or in divided doses.

The compounds of this invention may also be used as medicine for fish diseases, agricultural chemicals or food preservatives.

The processes for producing the novel compounds of the invention and their pharmacological activities are illustrated below.

Reference Example 1 shows a process for the preparation of the starting compound.

Examples 1 and 2 illustrate processes for the preparation of the compounds of this invention.

Experimental A to C show the pharmacological activities of the compound of the invention in comparison with those of compounds outside the scope of the invention as controls.

Examples 3 and 4 show the preparations of pharmaceuticals containing the compound of this invention.

EXAMPLE 1

Preparation of the compound 1

A mixture of 6-fluoro-1-(2-fluoroethyl)-1,4-dihydro-4-oxo-7-(1-piperazinyl)-1,8-naphthyridine-3-carboxylic acid (3.0 g), 37% formalin (4 ml) and formic acid (9 ml) is heated at 110° C. for 16 hours with stirring. The reaction mixture is concentrated to dryness under reduced pressure. The residue is dissolved in 10% aqueous ammonia, treated with active charcoal, and filtered. The filtrate is adjusted to pH 8–8.5 with 10% hydrochloric acid. The precipitate is collected by filtration, and recrystallized from acetonitrile to give 2.67 g of 6-fluoro-1-(2-fluoroethyl)-1,4-dihydro-7-(4-methyl-1-piperazinyl)-4-oxo-1,8-naphthyridine-3-carboxylic acid (compound 1), m.p. 224°–226° C.

REFERENCE EXAMPLE 1

Preparation of the starting compound (1) 2,6-Dichloropyridine is nitrated with fuming nitric acid and concentrated sulfuric acid. The product, 2,6-dichloro-3-nitropyridine, is allowed to react with N-acetyl-piperazine in chloroform to give 2-(4-acetyl-1-piperazinyl)-6-chloro-3-nitropyridine (m.p. 137°–138° C.). The compound obtained is treated with aqueous ammoniaethanol in an autoclave to give 2-(4-acetyl-1-piperazinyl)-6-amino-3-nitropyridine (m.p. 202°–203° C.), which is then acetylated with acetic anhydride in acetic acid to give 6-acetylamino-2-(4-acetyl-1-piperazinyl))-3-nitropyridine (m.p. 189°–193° C., 221°–223° C.).

The above 6-acetylamino compound is dissolved in a mixture of acetic acid and ethanol, and reduced by adding zinc powder. Without purification, the resulting compound, 3-amino-6-acetylamino-2-(4-acetyl-1-piperazinyl)pyridine, is dissolved in a mixture of 42% tetrafluoroboric acid and ethanol. To this solution is added an aqueous solution of sodium nitrite under cooling and 6-acetylamino-2-(4-acetyl-1-piperazinyl) pyridine-3-diazonium tetrafluoroborate (m.p. 121°–124° C.) is obtained.

A suspension of the above diazonium salt in cyclohexane is heated under reflux to give 6-acetylamino-2-

(4-acetyl-1-piperazinyl)-3-fluoropyridine (m.p. 178°–179.5° C.). This compound is added to a mixture of 10% hydrochloric acid and methanol, and hydrolyzed to give 6-amino-2-(4-acetyl-1-piperazinyl)-3-fluoropyridine (m.p. 116°–118° C.).

(2) A mixture of 6-amino-2-(4-acetyl-1-piperazinyl)-3-fluoropyridine (23.9 g) and diethyl ethoxymethylenemalonate (22.7 g) is heated for 5 hours with stirring. After cooling, the precipitate is collected by filtration, and recrystallized from ethanol to give 35.5 g of diethyl N-[6-(4-acetyl-1-piperazinyl)-5-fluoro-2-pyridyl]aminomethylenemalonate (m.p. 164°–165° C.).

A mixture of the above malonate (30.6 g) and Dowtherm A (a trade name for a product of Dow Chemical Co., 300 ml) is heated at 249°–250° C. for 20 minutes. After cooling to room temperature, acetone (120 ml) is added to the mixture with stirring. The resulting crystals are collected by filtration, recrystallized from dimethylformamide to give 16.6 g of ethyl 7-(4-acetyl-1-piperazinyl)-6-fluoro-1,4-dihydro-4-oxo-1,8-naphthyridine-3-carboxylate (m.p. 290°–295° C.).

(3) Ethyl 7-(4-acetyl-1-piperazinyl)-6-fluoro-1,4-dihydro-4-oxo-1,8-naphthyridine-3-carboxylate (7.2 g) and anhydrous potassium carbonate (4.1 g) are added to dimethylformamide (60 ml). The mixture is heated at 50° C. for 30 minutes with stirring. 2-Fluoroethyl p-toluenesulfonate (6.5 g) is added to the mixture, and the mixture is heated at 70°–80° C. with stirring. After the reaction is completed, the insoluble substance is removed by filtration. The filtrate is concentrated to dryness under reduced pressure, and the precipitate is collected by filtration. The precipitate is recrystallized from acetone to give 6.3 g of ethyl 7-(4-acetyl-1-piperazinyl)-6-fluoro-1-(2-fluoroethyl)-1,4-dihydro-4-oxo-1,8-naphthyridine-3-carboxylate (m.p. 183°–185° C.).

A suspension of the above ester (4.8 g) in 10% hydrochloric acid (48 ml) is heated for 2 hours on a steambath. After cooling, an appropriate amount of ethanol is added to the mixture to precipitate crystals, which are collected by filtration, dissolved in water (about 50 ml), treated with active charcoal, and filtered. The filtrate is adjusted to pH 7.5–8 with 10% aqueous ammonia to give 3.5 g of 6-fluoro-1-(2-fluoroethyl)-1,4-dihydro-4-oxo-7-(1-piperazinyl)-1,8-naphthyridine-3-carboxylic acid (m.p. 223°–225° C.).

EXAMPLE 2

Preparation of compound 2

Using 6-fluoro-1-(2-fluoroethyl)-1,4-dihydro-4-oxo-7-(1-piperazinyl)-1,8-naphthyridine-3-carboxylic acid as a starting material, by reaction with acetoaldehyde in the presence of formic acid in accordance with the method of Example 1 is obtained 7-(4-ethyl-1-piperazinyl)-6-fluoro-1-(2-fluoroethyl)-1,4-dihydro-4-oxo-1,8-naphthyridine-3-carboxylic acid (compound 2) m.p. 223°–224° C.

Experiment A

The minimum inhibitory concentrations (MIC: μg/ml) of the following compounds were measured by the agar dilution method according to the procedure described in Chemotherapy, Vol. 22, No. 16, page 1126 (1974).

The results are shown in Table I.

Compound 1

6-Fluoro-1-(2-fluoroethyl)-1,4-dihydro-7-(4-methyl-1-piperazinyl)-4-oxo-1,8-naphthyridine-3-carboxylic acid

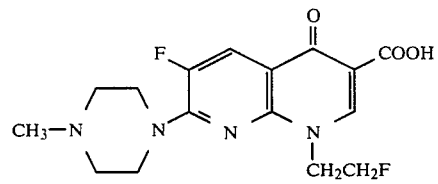

(the compound obtained by the procedure discribed in Example 1).

Compound A

1-Ethyl-6-fluoro-1,4-dihydro-7-(4-methyl-1-piperazinyl)-4-oxo-1,8-naphthyridine-3-carboxylic acid

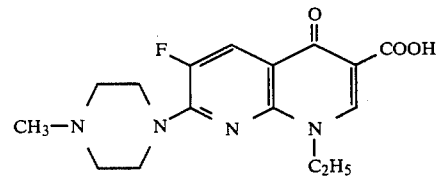

(the compound disclosed in European Laid-open Patent Application No. 0009425).

Compound B

6-Fluoro-1-(2-fluoroethyl)-1,4-dihydro-4-oxo-7-(1-piperazinyl)-1,8-naphthyridine-3-carboxylic acid

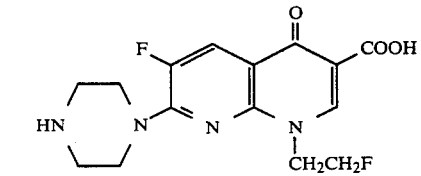

(the compound disclosed in Japanese Laid-Open Patent Application No. 31042780).

TABLE I

In vitro antibacterial activity against 19 strains of bacteria

| Bacteria | | Compound | | |
|---|---|---|---|---|
| | | 1 | A | B |
| Staphylococcus aureus 209P JC-1 | Gram-positive bacteria | 0.78 | 1.56 | 0.39 |
| Staphylococcus aureus No. 50774 | | 0.39 | 1.56 | 1.56 |
| Streptococcus faecalis P-2473 | | 12.5 | 12.5 | 12.5 |
| Streptococcus pyogenes A65 | | 12.5 | 6.25 | 12.5 |
| Corynebacterium pyogenes C-21 | | 6.25 | 6.25 | 1.56 |
| Escherichia coli NIHJ JC-2 | | 0.2 | 0.39 | 0.2 |
| Escherichia coli P-5101 | | 0.1 | 0.2 | 0.1 |
| Escherichia coli P-140a | | 0.1 | 0.39 | 0.1 |
| Salmonella typhimurium S-9 | | 0.2 | 0.2 | 0.1 |
| Salmonella | | 0.1 | 0.1 | 0.1 |

TABLE I-continued

In vitro antibacterial activity
against 19 strains of bacteria

| Bacteria | Compound 1 | A | B |
|---|---|---|---|
| enteritidis No. 1891 | | | |
| Shigella flexneri 2a | 0.39 | 0.39 | 0.2 |
| Shigella flexneri 4a P-330 | 0.1 | 0.78 | 0.1 |
| Klebsiella pneumoniae No. 13 | 0.39 | 0.39 | 0.78 |
| Enterobacter cloacae P-2540 | 0.2 | 0.39 | 0.1 |
| Pseudomonas aeruginosa Tsuchijima | 3.13 | 1.56 | 0.78 |
| Pseudomonas aeruginosa No. 12 | 1.56 | 3.13 | 0.78 |
| Serratia marcescens IFO 3736 | 1.56 | 1.56 | 0.39 |
| Proteus morganii Kono | 0.39 | 0.78 | 0.2 |
| Proteus mirabilis P-2381 | 0.78 | 3.13 | 0.39 |

Experiment B

In vivo therapeutic efficacy against systemic infections in mice

Compound 1 of this invention obtained by the procedure described in Example 1 and compounds A and B were each suspended in a 0.2% aqueous solution of sodium carboxymethylcellulose. Each of the solutions was orally administered to mice infected with each of the test organisms under the conditions described below, and the median effective doses ($ED_{50}$; mg/kg) obtained are shown in Table II.

Experimental conditions

Mice

Male mice (ddY) weighing about 20 g

Infection (1) *Staphylococcus aureus* No. 50774: Intravenous infection with about $5 \times 10^8$ cells per mouse suspended in saline.
(2) *Streptococcus pyogenes* A65 Intraperitoneal infection with about $3 \times 10^7$ cells per mouse suspended in brain-heart infusion broth.
(3) *Escherichia coli* P-5101: Intraperitoneal infection with about $9 \times 10^6$ cells per mouse suspended in trypto-soy broth with 4% mucin.
(4) *Pseudomonas aeruginosa* No. 12: Intraperitoneal infection with about $4 \times 10^3$ cells per mouse suspended in trypto-soy broth with 4% mucin.

Medication

Twice, about 5 minutes and 6 hours after infection.

Observation

| | |
|---|---|
| *Staphylococcus aureus* No. 50774 | for 14 days |
| *Streptococcus pyogenes* A65 | |
| *Escherichia coli* P-5101 | for 7 days |
| *Pseudomonas aeruginosa* No. 12 | |

TABLE II

In vivo efficacy against systemic infections in mice

| | Bacterium | | | |
|---|---|---|---|---|
| | Staphylococcus aureus No. 50774 | Streptococcus pyogenes A65 | Escherichia coli P-5101 | Pseudomonas aeruginosa No. 12 |
| | Route | | | |
| Compound | po | po | po | po |
| 1 | 1.4 | 14.9 | 0.52 | 4.2 |
| A | 4.8 | >50 | 1.2 | 10.6 |
| B | 11.5 | 50 | 3.0 | 27.2 |

Note: The numerals in the table show $ED_{50}$ (mg/kg).
$ED_{50}$ values were calculated in accordance with the Behrens-Kaerber method [Arch. Exp. Path. Pharm., 162, 480 (1931)].
po: oral administration.

Experiment C

Acute oral toxicity in mice

A suspension containing each of compound 1 of the invention and compound A in various concentrations was orally given to male mice (ddY) at a volume of 0.1 ml per 10 g of body weight. The number of dead mice was counted after 7 days, and the value of median lethal dose ($LD_{50}$, mg/kg) was calculated in accordance with the Behrens-Kaerber method. The results are shown in Table III.

TABLE III

Acute oral toxicity in mice

| Compound | $LD_{50}$ (mg/kg) |
|---|---|
| 1 | >1,800 |
| A | 210 |

EXAMPLE 3

Compound 1—250 g
Starch—50 g
Lactose—35 g
Talc—15 g

The above components were blended and granulated and filled into 1,000 capsules in accordance with conventional methods.

EXAMPLE 4

Compound 1—250 g
Starch—54 g
Calcium carboxymethyl cellulose—40 g
Microcrystalline cellulose—50 g
Magnesium stearate—6 g The above components were blended, granulated and made into tablets in a manner known per se. Thus, 1,000 tablets each weighing 400 mg were formed.

What we claim is:
1. A 1,8-naphthyridine compound of the formula

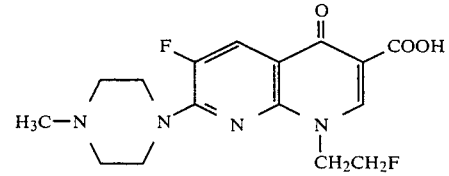

or a non-toxic pharmaceutically acceptable salt thereof.

2. A pharmaceutical composition which comprises an antibacterially effective amount of a 1,8-naphthyridine compound of the formula

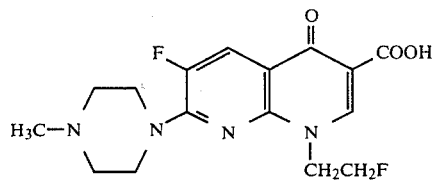

or a non-toxic pharmaceutically acceptable salt thereof and a pharmaceutically acceptable carrier or adjuvant.

3. A method for the treatment of a bacterial infectious disease which comprises administering to a warm-blooded animal suffering from such disease an antibacterially effective amount of a 1,8-naphthyridine compound of the formula

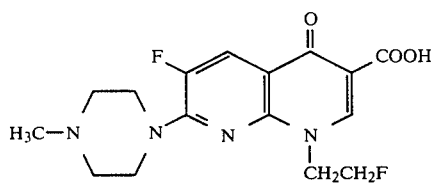

or a non-toxic pharmaceutically acceptable salt thereof.

* * * * *

UNITED STATES PATENT AND TRADEMARK OFFICE
CERTIFICATE OF CORRECTION

PATENT NO. : 4,496,566

DATED : January 29, 1985

INVENTOR(S) : Jun-ichi MATSUMOTO; Shinichi NAKAMURA

It is certified that error appears in the above-identified patent and that said Letters Patent is hereby corrected as shown below:

Column 4, line 51, change "ammoniaethanol" to --ammonia-ethanol--.

Column 5, line 12, change "pyridyl)aminomethylenemalonate" to --pyridyl]aminomethylenemalonate--.

Column 6, line 46, change "No. 31042780" to --No. 31042/80--;

correct the portion of TABLE I appearing at lines 48 to 68 to read as follows:

TABLE I

In vitro antibacterial activity against 19 strains of bacteria

| Bacteria | | Compound 1 | A | B |
|---|---|---|---|---|
| Staphylococcus aureus 209P JC-1 | Gram-positive bacteria | 0.78 | 1.56 | 0.39 |
| Staphylococcus aureus No. 50774 | | 0.39 | 1.56 | 1.56 |
| Streptococcus faecalis P-2473 | | 12.5 | 12.5 | 12.5 |
| Streptococcus pyogenes A65 | | 12.5 | 6.25 | 12.5 |
| Corynebacterium pyogenes C-21 | | 6.25 | 6.25 | 1.56 |
| Escherichia coli NIHJ JC-2 | Gram-negative bacteria | 0.2 | 0.39 | 0.2 |
| Escherichia coli P-5101 | | 0.1 | 0.2 | 0.1 |
| Escherichia coli P-140a | | 0.1 | 0.39 | 0.1 |
| Salmonella typhimurium S-9 | | 0.2 | 0.2 | 0.1 |
| Salmonella enteritidis No. 1891 | | 0.1 | 0.1 | 0.1 |

UNITED STATES PATENT AND TRADEMARK OFFICE
CERTIFICATE OF CORRECTION

PATENT NO. : 4,496,566

DATED : January 29, 1985

INVENTOR(S) : Jun-ichi MATSUMOTO; Shinichi NAKAMURA

It is certified that error appears in the above-identified patent and that said Letters Patent is hereby corrected as shown below:

Column 7, the portion of TABLE I appearing at lines 1 to 23, correct to read as follows:

TABLE I-continued

In vitro antibacterial activity against 19 strains of bacteria

| Bacteria | | Compound 1 | A | B |
|---|---|---|---|---|
| Shigella flexneri 2a | | 0.39 | 0.39 | 0.2 |
| Shigella flexneri 4a P-330 | | 0.1 | 0.78 | 0.1 |
| Klebsiella pneumoniae No. 13 | | 0.39 | 0.39 | 0.78 |
| Enterobacter cloacae P-2540 | Gram-negative bacteria | 0.2 | 0.39 | 0.1 |
| Pseudomonas aeruginosa Tsuchijima | | 3.13 | 1.56 | 0.78 |
| Pseudomonas aeruginosa No. 12 | | 1.56 | 3.13 | 0.78 |
| Serratia marcescens IFO 3736 | | 1.56 | 1.56 | 0.39 |
| Proteus morganii Kono | | 0.39 | 0.78 | 0.2 |
| Proteus mirabilis P-2381 | | 0.78 | 3.13 | 0.39 |

UNITED STATES PATENT AND TRADEMARK OFFICE
CERTIFICATE OF CORRECTION

PATENT NO. : 4,496,566

DATED : January 29, 1985

INVENTOR(S) : Jun-ichi MATSUMOTO; Shinichi NAKAMURA

It is certified that error appears in the above-identified patent and that said Letters Patent is hereby corrected as shown below:

Column 8, line 16, change "Pharm., 162" to read --Pharm., 162--.

Signed and Sealed this

Twenty-fourth Day of September 1985

[SEAL]

Attest:

Attesting Officer

DONALD J. QUIGG

Commissioner of Patents and Trademarks—Designate